United States Patent [19]
Lefebvre

[11] Patent Number: 5,108,418
[45] Date of Patent: Apr. 28, 1992

[54] DEVICE IMPLANTED IN A VESSEL WITH LATERAL LEGS PROVIDED WITH ANTAGONISTICALLY ORIENTED TEETH

[76] Inventor: Jean-Marie Lefebvre, 219, boulevard de la liberté59800 Lille, France

[21] Appl. No.: 595,191

[22] Filed: Oct. 10, 1990

[30] Foreign Application Priority Data

Mar. 28, 1990 [FR] France ............... 90 04552

[51] Int. Cl.⁵ ............................................. A61B 17/00
[52] U.S. Cl. ...................................... 606/200; 210/448
[58] Field of Search ............... 606/191, 195, 194, 200, 606/152-156, 198; 128/899; 623/1, 12; 210/448; 604/104

[56] References Cited

U.S. PATENT DOCUMENTS

| | | | |
|---|---|---|---|
| 2,281,448 | 4/1942 | Mathey | 210/448 |
| 3,540,431 | 11/1970 | Mobin-Uddin | 606/200 |
| 3,815,578 | 6/1974 | Bucalo | 606/153 |
| 3,952,747 | 4/1976 | Kimmell, Jr. | 606/200 |
| 4,688,553 | 8/1987 | Metals | 606/200 |
| 4,817,600 | 4/1989 | Herms et al. | 606/198 |
| 4,990,156 | 2/1991 | Lefebvre | 606/191 |

FOREIGN PATENT DOCUMENTS 2570288 3/1986 France .

Primary Examiner—C. Fred Rosenbaum
Assistant Examiner—William Lewis
Attorney, Agent, or Firm—Ladas & Parry

[57] ABSTRACT

This invention relates to a device adapted to be implanted in a vessel, for example a filter for retaining blood clots in a vein, which comprises lateral legs abutting on the wall of the vessel. According to the invention, each leg, whose end is not sharp, is provided with at least two teeth with antagonistic inclination. They are preferably placed towards the rounded end of the leg and have divergent directions. The tooth is for example obtained by cutting out and pushing a median part of the leg, and possibly by subsequent bending thereof. The angle made by the end part of the tooth with respect to the plane of the leg is included between 0 and 30°; the tip of the tooth is at a distance of between 0.8 and 2 mm from the leg.

7 Claims, 1 Drawing Sheet

5,108,418

DEVICE IMPLANTED IN A VESSEL WITH LATERAL LEGS PROVIDED WITH ANTAGONISTICALLY ORIENTED TEETH

FIELD OF THE INVENTION

The present invention relates to devices adapted to be implanted definitively in a vessel and which comprise lateral legs abutting on the inner wall of said vessel; it concerns in particular filters introduced by the endovenous route to prevent the migration of blood clots. More precisely, the present invention concerns the hooking means with which the legs are provided and which ensure anchoring of the device in the wall of the vessel.

BACKGROUND OF THE INVENTION

In the known devices, the hooking means present various shapes, which are a function of the configuration of the legs. In documents FR.A.2 570 288 and U.S. Pat. No. A.3 952 747, they are constituted by the sharp end of each leg which is bent to form a hook. In U.S. Pat. No. A.3 334 629, it is question of a plurality of small teeth projecting from the outer surface of the free end of each leg.

The purpose of these hooking means is to maintain the device at the place where it was implanted in the vessel, avoiding any displacement and any migration of the device, and also avoiding perforation of or injury to the wall of the vessel.

According to Applicant, this purpose is only imperfectly attained in the prior art devices. He has observed that, being designed to oppose any displacement of the device in the direction of blood flow within the vessel, the hooking means mentioned above are not really in a position to ensure definitive and absolute anchoring. In fact, the wall of the vessel is not a rigid element; it is subjected to fluctuating movements during passage of the flow, in particular of the blood flow in a vein. These fluctuating movements act on the legs of the device and may cause unhooking of all or part of these legs of which the hooks or teeth all have the same orientation, with, correlatively, a displacement of the whole device or a relative displacement of one or more legs with respect to the others and therefore a poor positioning of the device with respect to the vessel. These fluctuating movements may, in combination with the driving force of the flux, also cause perforation of the wall when the hooking means are too sharp.

SUMMARY OF THE INVENTION

The purpose set forth hereinabove is perfectly attained by the device of the invention, adapted to be implanted definitively in a vessel, for example a filter for retaining blood clots, and which comprises lateral legs provided with hooking means. According to the invention, the end of the leg is not sharp and the hooking means consist of at least two teeth oriented antagonistically, in the general direction of the leg.

The term "tooth" must here be taken in a general sense, as being a rod projecting from the surface of the leg, of which one end is fast with the leg and the other end is pointed.

Each leg comprises two teeth which are inclined with respect to the surface of the leg, one in the direction of flow of the blood and the other in the opposite direction. Thanks to this particular arrangement, the fluctuating movements of the wall cause the two teeth to hook in the wall. Once such hooking is effected, it opposes any movement of the leg in one direction and in the other; the anchoring obtained is really definitive and absolute. As the end of the legs is not sharp, there is no risk of direct penetration of the legs in the wall.

When that part of the leg which abuts on the wall of the vessel is of reduced length, from one to some centimetres, it is necessary that the two teeth be near each other; however, in that case, in order to obtain the desired effect, it is desirable that their directions be divergent. In the contrary case, the space between the pointed ends would be too small for the wall of the vessel to be able to be introduced therein during opening of the device and application of the legs on the wall.

In order to avoid the risks of perforations of the wall, whilst ensuring efficient anchoring, it is preferable if the structure of the tooth with respect to the leg be such that at least the free end of the tooth has an inclination with respect to the leg of, at the most, 30°, the tip of the tooth being at a distance of between 0.8 and 2 mm from the leg. In this way, the tooth can penetrate in the wall only by a reduced thickness.

This may be obtained with a rectilinear tooth; however, in order to limit the length of the tooth, it is advantageous if the tooth is curved or bent, its end fast with the leg having an inclination greater than 30°.

In the preferred embodiment, each leg of the device being a flat metal rod, the teeth are obtained by cut-out and pushing in the median part close to the free end of the rod.

Each leg is preferably provided with two teeth having the form of two triangles of which the parallel bases, fast with the leg, are spaced apart by a distance of between 2 and 10 mm.

BRIEF DESCRIPTION OF THE DRAWINGS

The invention will be more readily understood on reading the following description of an embodiment of a medical filter for retaining blood clots, of which each lateral leg is provided with two antagonistically oriented teeth, with reference to the accompanying drawings, in which.

DETAILED DESCRIPTION OF THE DRAWINGS

Figure 1:
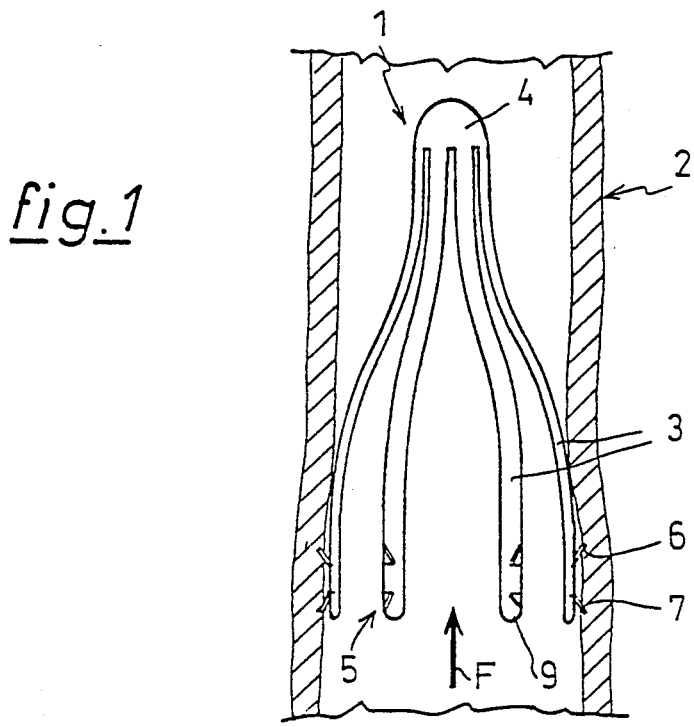
FIG. 1 is a side view of a filter.

Referring now to the drawings, the filter 1 shown in FIG. 1 is placed inside a vein 2 in which the blood flows in the direction of arrow F. Filter 1 is generally conical in shape, with lateral legs 3 which are joined to form the ogival head 4 of the filter. The free ends 5 of each lateral leg 3 present a rounded end 9 and comprise two teeth 6, 7.

The filter is made, in conventional manner, of a material which presents a certain elasticity, with the result that the legs 3 may be brought substantially against one another in a sheath for introduction, of the catheter type, and that they open out inside the vein 2 when the filter is pushed out of the sheath. The elastic deformation of the legs 3 with respect to the ogival head 4 is such that, the filter 1 being implanted, the free end 5 of each lateral leg 3 abuts on the inner wall 8 of the vein 2.

According to the preferred embodiment, the filter 1 is a metal piece with six flat rods acting as legs 3. Each leg 3 has a width of the order of 2 mm.

Figure 2:
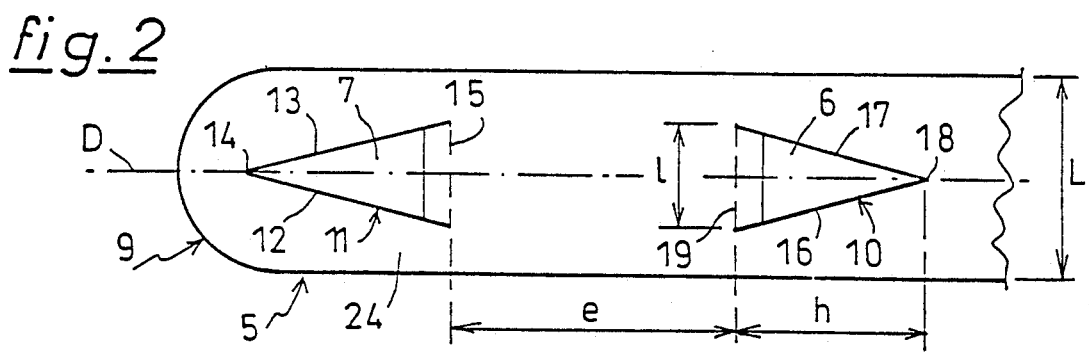
FIG. 2 is a plan view of the end of a leg.

FIG. 2 shows the free end 5 of a leg 3, with its rounded end 9. To produce teeth 6, 7, two cut-outs are made along solid lines 10, 11. Cut-out 11 corresponding to tooth 7, located in the immediate vicinity of the end 9, is formed by two rectilinear cuts 12, 13 intersecting at a point 14 lying on the axis of symmetry D of leg 3. Point 14 is located towards the rounded end 9. An examination of FIG. 2 will show that tooth 7 is obtained by pushing the triangular part defined by cuts 12, 13, outwardly of leg 3. The broken line 15 constitutes the axis of fold and therefore the base of tooth 7, rendering the latter fast with leg 3.

Cuts 16, 17 corresponding to the second cut-out 10 are effected in the same manner as hereinabove, except that the point of convergence 18 of the two cuts 16, 17 faces the ogival head 4.

In a precise example, the free end 5 of the leg 3 having a width $\underline{L}$ of 2 mm, the bases 15 and 19 of the two teeth have a length $\underline{1}$ of 1 mm; they are parallel to and spaced apart from each other by a distance $\underline{e}$ of 2.5 mm. The height $\underline{h}$ of the triangle corresponding to the theoretical height of the tooth is 1.8 mm.

Figure 3:
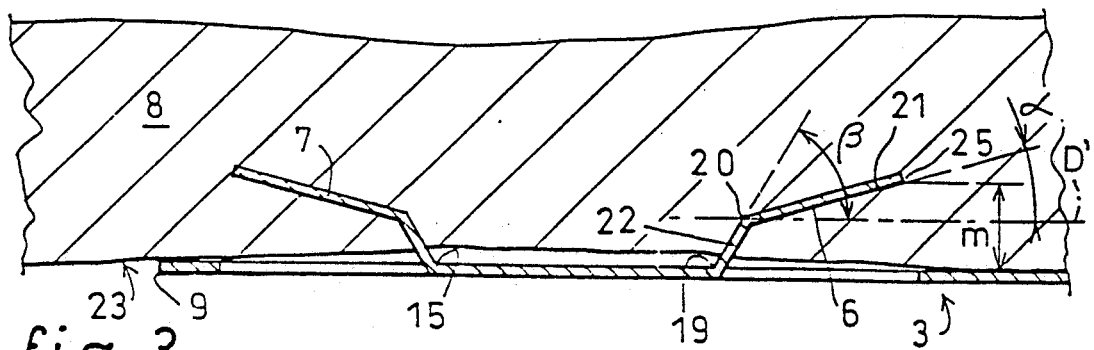
FIG. 3 is a view in longitudinal section of the end of a leg hooked on a vein wall.

Each tooth 6, 7 is bent, as shown in FIG. 3, along an axis of bend 20 which separates, on the one hand, the triangular end part 21 of the tooth and, on the other hand, that part 22 joining the leg 3, forming an isosceles trapezium of which the large base is the first line 19 along which the part inside the two cuts 16, 17 was pushed.

The angle $\alpha$ formed between the triangular end part 21 of the tooth and the direction D' of the plane of the leg 3 is preferably included between 0° and 30°; in the example mentioned above, it is 15°.

The angle $\beta$ formed between the trapezoidal part 22 of the tooth and the direction D' of the plane of the leg 3 is preferably included between 45 and 90°; in the example mentioned above, it is 60°.

The tip 25 of tooth 6 is distant by a height $\underline{m}$ from the leg 3, which is preferably included between 0.8 and 2 mm. In the example mentioned above, it is 1 mm.

When the filter is placed in the vein 2, the legs 3 open out and their ends 5 are applied on the inner face 23 of the wall 8. Under the driving force of the blood flow, the filter 1 tends to move in the direction of arrow F, which causes the tooth 6 facing the ogival head 4 to penetrate in the vein wall 8. Moreover, the fluctuating movements of the wall 8 promote progressive penetration of the tooth 7 facing the rounded end 9. The surface 24 of the free end 5 of the leg 3 forms a large bearing surface which prevents any penetration of the leg 3 itself in the wall 8.

In this way, after the teeth 6, 7 of all the legs 3 have penetrated in the wall 8 of the vein 2, the filter 1 is definitively hooked without any possibility of subsequent migration and without risk of injuring the vein 2.

The invention is not limited to the embodiment which has been described by non-limiting example, although this is the preferred embodiment, but it covers all the variants thereof. In particular, the total number of teeth on each leg is not necessarily two; what is important is that there are at least two antagonistically oriented teeth. Furthermore, the man skilled in the art can determine, as a function of the type of device, filtering, blocking or spacing apart, as a function of its dimensions and the constituent materials, the configuration and arrangement of the antagonistically oriented teeth. It will be understood that a result similar to the bend along line 20 may be obtained by curving the tooth along an arc of circle, so that the outermost part of the tooth makes with the direction of the plane of the leg an angle $\alpha$. Similarly, the term leg is not exclusive of the legs serving for filtration or spacing apart; it may also be question of the appendices provided in document FR.A.2 573 646, which constitute, to some extent, the free ends which abut on the wall of the vessel, in the sense given in the present specification.

What is claimed is:

1. A filter device adapted to be implanted into a vessel or lumen of the body, comprising a head and a plurality of legs extending from the head, free ends of said legs being rounded, and hooking means provided on each of the legs, said hooking means including at least two teeth oriented antagonistically in a longitudinal direction of the leg.

2. The device of claim 1 wherein the two teeth of the hooking means are in the vicinity of each other and have divergent directions.

3. The device of claim 1 or claim 2, wherein a free end of each said tooth of the hooking means presents a inclination with respect to the leg of at the most 30° and a tip of the free end of the tooth is at a distance of between 0.8 and 2 mm from the leg.

4. The device of claim 3, wherein the tooth is of a curved or bent portion fast with the leg presenting an inclination greater than 30°.

5. The device of claim 4, wherein the inclination of the bend portion of the tooth fast with the leg is between 45° and 20 .

6. The device of claim 1, wherein, each leg being a flat metal rod, the teeth of the hooking means are obtained by cutting out from the leg and pushing in the median part.

7. The device of claim 1, wherein each leg is provided with two teeth shaped as two triangles whose parallel bases, fast with the leg, are spaced apart by a distance of between 2 and 10 mm.

* * * * *